(12) United States Patent
Hauch et al.

(10) Patent No.: US 8,557,528 B2
(45) Date of Patent: *Oct. 15, 2013

(54) DETECTION OF TUMOR STEM CELLS AND TUMOR CELLS IN EPITHELIAL-MESENCHYMAL TRANSITION IN BODY FLUIDS OF CANCER PATIENTS

(75) Inventors: Siegfried Hauch, Coppenbrügge (DE); Albert Winfried, St. Gilgen (AT)

(73) Assignee: Adnagen GmbH, Langenhagen (DE)

( * ) Notice: Subject to any disclaimer, the term of this patent is extended or adjusted under 35 U.S.C. 154(b) by 425 days.

This patent is subject to a terminal disclaimer.

(21) Appl. No.: 12/678,712

(22) PCT Filed: Sep. 17, 2008

(86) PCT No.: PCT/EP2008/007775
§ 371 (c)(1),
(2), (4) Date: Jun. 16, 2011

(87) PCT Pub. No.: WO2009/036968
PCT Pub. Date: Mar. 26, 2009

(65) Prior Publication Data
US 2011/0236904 A1    Sep. 29, 2011

(30) Foreign Application Priority Data

Sep. 17, 2007 (EP) .................................. 07018205
May 9, 2008 (EP) .................................. 08008770

(51) Int. Cl.
*G01N 33/53* (2006.01)
(52) U.S. Cl.
USPC ............. 435/7.1; 435/378; 435/366; 435/325
(58) Field of Classification Search
USPC .................................. 435/7.1, 366, 378, 325
See application file for complete search history.

(56) References Cited

U.S. PATENT DOCUMENTS 5,753,631 A * 5/1998 Paulson et al. .................. 514/25
2006/0141512 A1 * 6/2006 Sinha et al. ....................... 435/6

OTHER PUBLICATIONS

Demel et al., "Detection of Tumour Cells in the Peripheral Blood of Patients with Breast Cancer. Development of a New Sensitive and Specific Immunomolecular Assay," *J Exp Clin Cancer Res*, 23(3): 465-468, 2004.
Morgan et al., "The matrix effects on kinetic rate constants of antibody—antigen interactions reflect solvent viscosity," *Journal of Immunological Methods*, 217:51-60, 1998.
Müller et al., "Ligand Binding to Anti-Fluorescyl Antibodies: Stability of the Antigen Binding Site," *Biochemistry*, 33:6221-6227, 1994.
Olle et al., "Comparison of antibody array substrates and the use of glycerol to normalize spot morphology," *Experimental and Molecular Pathology*, 79: 206-209, 2005.
Zieglschmid et al., "Combination of Immunomagnetic Enrichment with Multiplex RT-PCR Analysis for Detection of Disseminated Tumor Cells," *Anticancer Research*, 25:1803-1810, 2005.

* cited by examiner

*Primary Examiner* — Susan Hanley
(74) *Attorney, Agent, or Firm* — Steptoe & Johnson LLP

(57) ABSTRACT

The present invention relates to the detection of tumor stem cells and tumor cells in epithelial-mesenchymal transition and uses of such methods.
According to the present invention said method comprises a selecting step for selection or enrichment of said predetermined cells from the sample wherein the sample is contacted with the solid surface for preferential binding of said predetermined cells to the solid surface and then the sample is removed from the solid surface in a washing step. The inventive method is characterized in that the sample contains a polyol at least during one of contacting the sample with the solid surface and the washing step and in a detection step detecting in said cells, preferentially selected or enriched by said selecting step, the presence or absence of expression of at least one marker associated with at least one of the group comprising tumor stem cells and tumor cells in epithelial-mesenchymal transition.

12 Claims, 6 Drawing Sheets

DETECTION OF TUMOR STEM CELLS AND TUMOR CELLS IN EPITHELIAL-MESENCHYMAL TRANSITION IN BODY FLUIDS OF CANCER PATIENTS

This application is a national phase application under 35 U.S.C. §371 of International Patent Application No. PCT/EP2008/007775 filed Sep. 17, 2008, which claims priority to European Patent Application No. EP07018205.0 filed Sep. 17, 2007 and European Patent Application No. EP08008770.3 filed May 9, 2008. The entire texts of each of the above-referenced disclosures is specifically incorporated herein by reference without disclaimer.

The biology of circulating tumor cells (CTC) can be assessed using various molecular biological methods (RT-PCR, real-time PCR, micro-chip technology). The determination of over-expressed pharmaceutical target genes (estrogen receptor, progesterone receptor, EGFR, HER2) might be helpful in the context of personalized strategies in cancer treatment. However, the global determination of signal transduction pathways that are altered in the cancer cell metabolism may lead to a better understanding how tumor cells are enabled to escape the immune system and to build up resistance against drug treatment. Recent key findings in primary tumor tissue suggest that the metastatic potential of a tumor is based on the presence of a number of stem cell like tumor cells that have been identified to be the active source of metastatic spread. Cancer stem cells detected in primary tumor tissue were found to be relevant for clinical outcome after treatment. Consequently, one can assume that such tumor stem cells are disseminated from the primary tumor into the circulation and escape therapy due to their stem cell properties until they reach their homing organ where they act as seed for metastasis formation. Cancer stem cells, enriched from the primary tumor, were found to stain positive for CD44 stem cell marker but negative for CD24. More recently also ALDH1 was found to be a specific marker for cancer stem cells. There is certain evidence that the circulating tumor cells might be identified partly as cancer stem cells due to similarities such as increased resistance to chemotherapy and decreased proliferation during circulation. Similar findings were reported for disseminated tumor cells in bone marrow where tumor cells with a stem cell like phenotype were demonstrated. There are no corresponding experimental results for CTC.

Furthermore, in addition to the cancer stem cell concept, it was hypothesized that tumor cells spread into the circulation may undergo phenotypical changes, known as epithelial-mesenchymal transition (EMT). These cells have reduced apoptosis and are drug resistant. This allows them to travel to the site of metastasis formation and prevents them from getting affected by conventional treatment. EMT is known to occur in embryonic development where epithelial cells must escape structural constraints imposed by tissue architecture. They achieve this by adopting a phenotype more amenable to cell movement. The progression of carcinomas to invasive and metastatic disease shows high similarities to this process. Previous epithelial tumor cells that may convert into mesenchymal phenotype could, therefore, escape the primary tumor tissue and develop resistance against conventional therapy regimens, like anti-hormone treatment, since they lost the relevant therapeutic targets during that transformation (own findings). On the other hand it might also be possible, that the expression of potential therapeutic targets, like the Her2-receptor, is induced in such cells, even if the primary tumor was found negative for these targets.

Due to the fact that metastazation requires a dissemination of tumor stem cells or tumor cells showing EMT, the detection and characterization of CTC that show an EMT or stem cell like metabolism could be a powerful diagnostic tool for the early determination of therapy failure or the potential risk of resistance to a given therapeutic intervention. There are many molecular markers, that are useful to determine cells with a potential stem cell character or such cells that are in EMT (Table 1).

TABLE 1

Examples for markers to detect and characterize EMT and tumor stem cells

| Markers relevant to characterize EMT | Markers relevant to characterize stem cell phenotype |
|---|---|
| Integrin alpha V beta 6 | FGF2 |
| N-cadherin | BMI1 |
| Vimentin | ALDH1 |
| Fibronectin | CD44 |
| Snail1, Snail2 | CD24 |
| Twist1 | KRT19 |
| Goosecoid | Twist1 |
| FOXC2 | BRCA1 |
| SOX 10 | PTEN |
| MMP-2, MMP3, MMP9 | MSI1 |
| Beta catenin | CD34 |
| SMAD | NOTCH |
| NK kappa-beta | Jagged1 |
| Akt2 | |
| PI3K alpha | |
| c-kit | |
| CD133 | |
| VEGF | |
| NOTCH | |
| E-cadherin | |
| Cyclin D | |
| TGF β | |
| Mesothelin | |
| SIP1 | |

Up to date it could not be shown if the detection of CTC showing stem cell or EMT characteristics will be a prognostic und predictive marker due to their tumorigenic potential. Although expression profiling experiments on CTC have been published, no data are available that are able to characterize circulating tumor stem cells or cells in EMT after immunomagnetic CTC enrichment from blood with the required specificity. This proved to be a big challenge since the detection and characterization of such cells in blood is complicated by the fact that molecular markers useful for that purpose are also expressed in activated B-lymphocytes and other mononuclear cells. An enrichment of CTC by, for instance immunomagnetic strategies is only possible if the markers chosen for that purpose are rather tumor specific und show a low level of illegitimate expression in mononuclear blood cells.

However, genes, necessary for tumor stem cell or EMT detection, are widely expressed in non-tumor mononuclear blood cells. The non-specific trapping of such cells leads to a high non-specific background that prevents the detection of CTC stem cell/EMT markers.

It is therefore the object of the present invention to provide a solid phase isolation, enrichment and/or detection method for isolating, enriching and/or detecting tumor stem cells and/or tumor cells, which tumor cells are in epithelial-mesenchymal transition, as well as uses thereof.

This object is solved by the method according to claim 1 and the uses according to claims 10 to 12. Further improvements of the inventive method are provided in the respective dependent claims.

The present invention uses a recently developed additive, in particular for a wash buffer (EP 07 018 205.0 by Adnagen AG, Langenhagen), to allow the elimination of contaminating non-target cells in the enrichment of CTC and, therefore, increase the purity of the enriched CTC substantially. The wash buffer of the present invention contains a polyol, used in particular before, during and/or after contacting the sample with a solid surface for separation of the sought-after cells from the sample. The polyol might comprise or consist of at least one of the group comprising sorbitol, sucrose, trehalose, mannitol, fructose, maltit, lactitol, xylitol and glycerol in an amount (v/v or w/V) of at least 1%, preferably at least 10%, preferably at least 20% preferably at least 30%, preferably at least 50%, preferably at least 60% in the buffer solution.

Surprisingly, it was found that the immunomagnetic CTC enrichment combined with said polyol, in particular as component of a wash buffer, enabled the detection of EMT markers in low numbers (5 cells) of cultured ovarian cancer cells spiked into 5 ml of healthy donor blood samples. Additionally, CTC with tumor stem cell character as well as cells expressing EMT markers could be detected specifically in blood of metastatic cancer patients. Most surprisingly, it turned out that patients with CTC, exhibiting detectable stem cell and EMT markers, were therapy resistant and had a reduced overall survival in comparison to patients not expressing or overexpressing these markers.

Selection or enrichment of tumor cells from the sample and detection of sought-after cells may be done according to the method as disclosed in EP 02 732 726.1 filed by Adnagen AG, Langenhagen, Germany. The disclosure of EP 02 732 726.1 as well as the disclosure of EP 07 018 205.0 is incorporated into this application by reference. As an alternative, selection, enrichment and/or detection can be done by other methods in accordance with claim 1, e.g. using the Cell Search™ kit of Immunicon Corp., Huntingdon Valley, Pa., USA.

In the following some examples of the present invention are described.

Therein, FIG. 1 shows a schematic overview of sample preparation and analysis;

EXEMPLARY METHOD TO ENRICH AND TO DETECT CTC (SEE FIG. 1)

Immunomagnetic enrichment of tumor cells via epithelial and tumor associated antigens was achieved using the test kit AdnaTest BreastCancerSelect (Adnagen AG, Langenhagen, Germany) Comprising three different antibodies specifically binding to antigens EMA (epithelial membrane antigen, MUC-1 and EpCAM (human epithelial antigen).

These antibodies against epithelial and tumor associated antigens were conjugated to magnetic beads (Dynabeads) for the binding to tumor cells in peripheral blood. The cells bound to the magnetic beads were recovered by a magnetic particle concentrator, washed several times in PBS or in a buffer composition according to this invention.

Washing steps to remove mononuclear blood cells and erythrocytes were performed with a wash buffer consisting of 10-50% (V/V) glycerol and 1-10%. (W/V) mannitol in PBS-buffer (phosphate-buffered saline): 9 g NaCl, 0.23 g $Na_2HPO_4$, 1.15 g $Na_2HPO_4$ per 1 water; ph 7.2-7.4); 23% (V/V) glycerol; 5% (W/V) mannitol.

For verification, assessment of tumor stem cell markers or markers for tumor cells in EMT was done using the AdnaTest BreastCancerSelect kit (Adnagen AG, Langenhagen, Germany). Thereby, the enriched cells were lysed for further analysis by a RT-PCR assay using the test kit AdnaTest BreastCancerSelect (Adnagen AG, Langenhagen, Germany) containing primers for amplification of sections of DNA sequences corresponding to Ga733-2, MUC1 and Her2. The c-DNA obtained using the AdnaTest BreastCancerSelect kit was tested by PCR for the presence of CTC (or spiked tumor cells) according to the manufacturer's instructions and, additionally, for Twist, Akt2, PI3KCA (multiplex) and ALDH1 (singleplex) expression for the assessment of EMT related and tumor stem-cell markers. For this purpose, cDNA was amplified with HotSTarTaq (Qiagen, Hilden, Germany) using multiplex primers. PCR conditions are given in Table 2.

TABLE 2

| PCR conditions | |
|---|---|
| EMT PCR Setup | PCR Conditions |
| 12.5 µl HotStarTaq mix | Annealing at 60° C. (30 s |
| 6.125 µl Water | Elongation at 72° C. (45 s) |
| 4 µl cDNA | Denaturation at 94° C. (30 s) |
| Aktin primer (0.1 µM) | Number of cycles: 36 |
| PI3Kα primer (0.1 µM) | |
| Akt2 primer (0.25 µM) | |
| Twist primer (0.25 µM) | |

EXAMPLE 1

Figure 1:
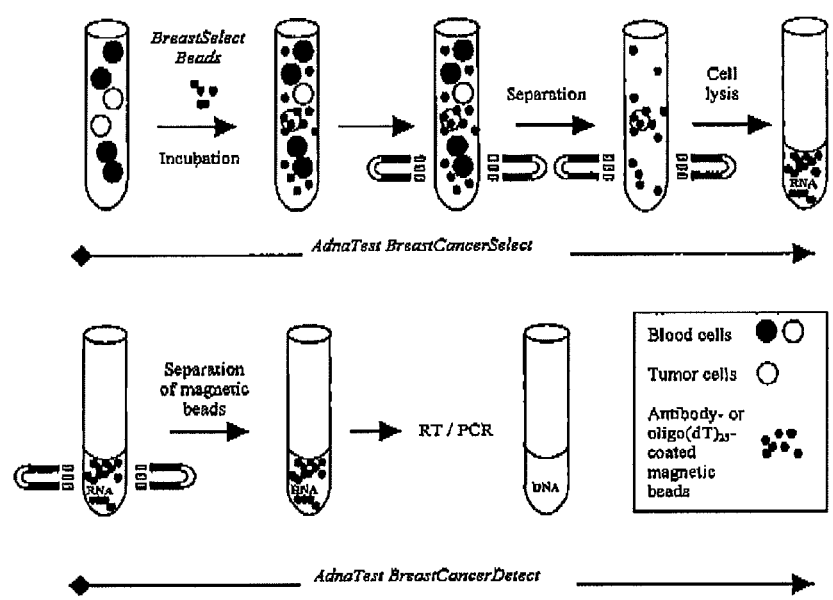
Figure 2:
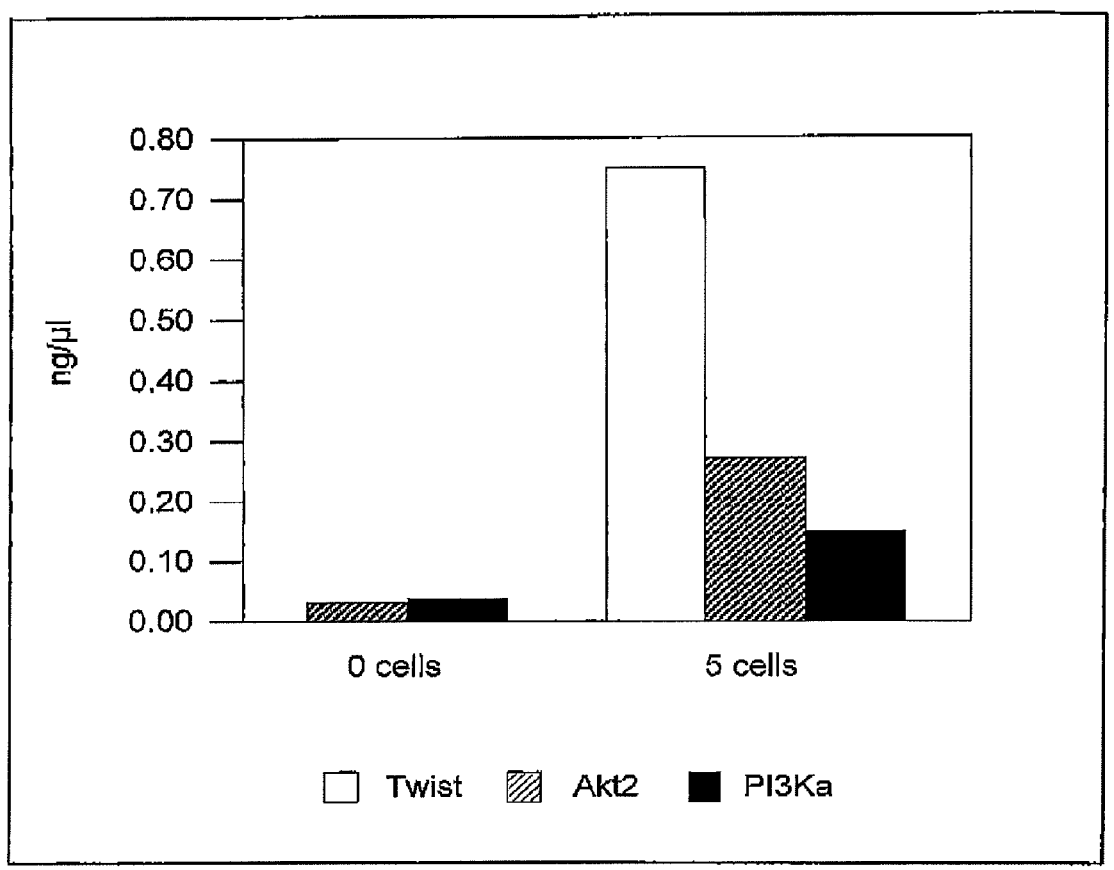
FIG. 2 shows detection of EMT markers in 5 ml blood sample spiked with 5 IGROV cells.

The test specificity and recovery (see FIG. 2) was assessed by the detection of target cells (0 or 5 IGROV-1 cells (ovarian cancer cell line, human; see Cancer Res 1985; 45; 4970-4979: PMID 3861241; spiked into 5 ml of healthy donor blood) with the AdnaTest BreastCancerDetect kit Three EMT associated genes (multiplex: Twist, Akt2, PI3KCA) and the tumor stem cell related ALDH1 gene were analyzed in a multiplex PCR set-up. The identification of EMT markers and/or the identification of tumor stem cell markers is considered positive if at least one marker is detected in the sample. Healthy donor samples without spiked tumor cells were used to determine specificity.

Applying a cut-off value of 0.2 ng/µl amplicon concentration none of the 10 HD samples were positive for any of the transcripts analyzed but the 5 spiked IGROV cells were detected positive in 9 of 10 samples resulting in 90% recovery.

EXAMPLE 2

Three markers related to EMT characteristics (Twist, Akt2, PI3KCA) were analyzed in CTC obtained from metastatic breast cancer patients previously confirmed by the AdnaTest BreastCancerSelect kit and AdnaTest BreastCancerDetect kit as CTC positive (see table 3). It could be clearly demonstrated that at least one or more of the markers were detectable in 8 out of 12 CTC positive patients (66%) but in only 12.5% of the CTC negative patients indicating a relationship of the EMT marker expression to the presence of CTC. This analysis indicates furthermore that a substantial amount of CTC found in the blood of cancer patients shows EMT characteristics. This leads to the conclusion that CTC expressing EMT markers are an indication for therapy resistant cell populations and, thus, for an inferior prognosis.

TABLE 3

The detection of EMT markers is restricted to CTC(+) samples.

| CTC status | EMT(+) | EMT(−) | Total |
|---|---|---|---|
| (+) | 8 | 4 | 12 |
| (−) | 2 | 14 | 16 |

EXAMPLE 3

A marker related to tumor stem cell characteristics (ALDFI1) was analyzed in CTC obtained from metastatic breast cancer patients previously confirmed by the AdnaTest BreastCancerSelect kit and the AdnaTest BreastCancerDetect kit as CTC positive (CTC(+)). It could be shown that ALDH1 expression was present in 5 out of 9 CTC positive patients (55%) but in only 20% of the CTC negative patients indicating a specific relationship of the tumor stem cell marker expression with the presence of CTC (see table 4). As in example 2, one can conclude that a substantial amount of CTC from the blood of cancer patients shows tumor stem cell characteristics and is an indicator for metastatic potential.

TABLE 4

The detection of ALDH1 is restricted to CTC(+) samples.

| CTC status | ALDH1+ | ALDH1− | Total |
|---|---|---|---|
| (+) | 5 | 4 | 9 |
| (−) | 2 | 8 | 10 |

EXAMPLE 4

Figure 3:
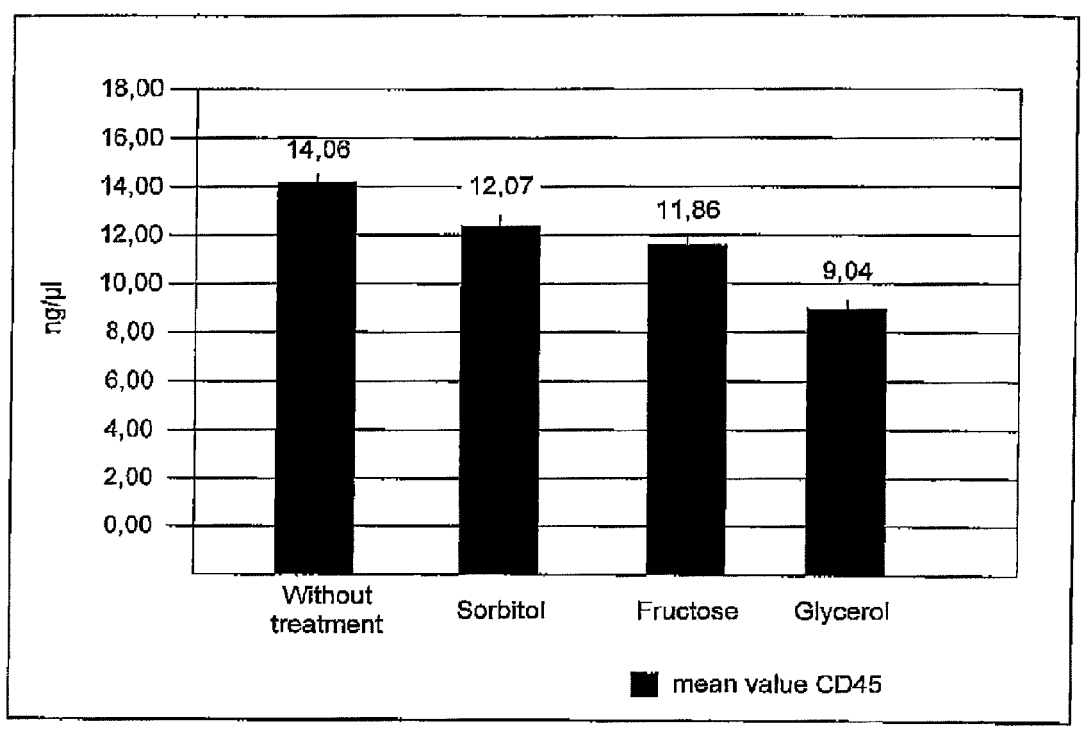
FIG. 3 shows the influence of different polyols in the washing buffer on leukocyte background.

The influence of different polyols in the washing buffer on leukocyte background was determined using sorbitol, fructose and glycerol as examples for polyols (see FIG. 3).

5 ml blood samples obtained from healthy donors were processed with AdnaTestBreastCancer Select followed by a CD45 RT-PCR. The washing steps were performed with PBS buffer containing one of said three polyols (sorbitol (W/V), fructose (W/V), glycerol (V/V)) at a concentration of 10%. PBS buffer without additive was used as a control and for an additional final wash of each sample before cell lysis and RT-PCR. As shown in FIG. 3, all polyols caused a reduction of CD45. Sorbitol and fructose caused about 15% and glycerol about 35% reduction of leukocyte background.

Obviously, as shown with these three arbitrarily selected polyols, all polyols are suitable for the present invention.

EXAMPLE 5

The detection of EMT and tumor cell markers is impeded by the high background signals produced by contaminating leukocytes.

To determine the effect of the AdnaWash buffer, containing the polyols glycerol (23% V/V) and mannitol (5% W/V) in PBS, healthy donor samples were processed with the AdnaT-est BreastCancerSelect reagents according to instruction with and without addition of this buffer. The cDNA obtained from these samples was analyzed by PCR for the EMT markers PI3KCA and Akt2 as well as for the tumor stem cell marker ALDH1.

Figure 4:
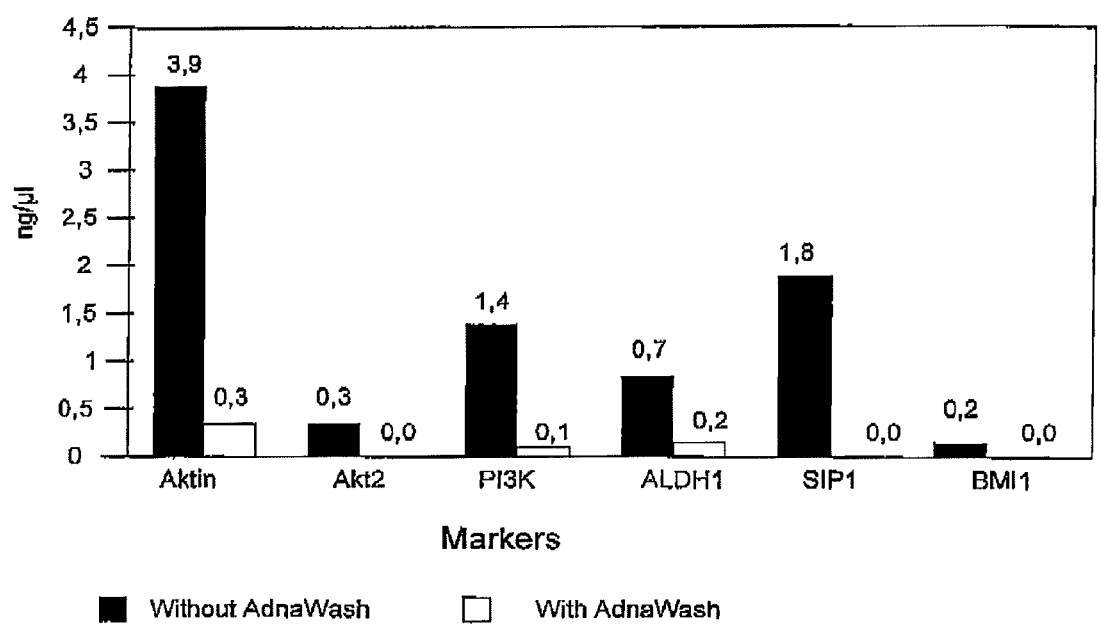
FIG. 4 shows the effect of polyols on leucocyte background for the isolation of tumor stem cells and EMT cells and subsequent detection of the relevant marker expression.

FIG. 4 shows that polyols decrease the leukocyte signals interfering with EMT (Akt2, Pi3KCA, SIP1) and tumor stem cell markers (BMI1, ALDH1) analysis due to removal of trapped leukocytes which is confirmed by the decrease of the actin signal.

By this example it is shown that trapped leukocytes express EMT and stem cell markers and produce unacceptable strong background signals. These signals could be efficiently reduced with a polyol containing washing buffer enabling a specific analysis of these markers on CTC. However, recovery of the CTC was not reduced.

EXAMPLE 6

Circulating tumor cells as indicator for bad prognosis and therapy failure over-express EMT and stem cell markers, when CTC positive and CTC negative metastatic breast cancer patient samples are compared.

The samples were processed with the AdnaTest BreastCancerSelect reagents according to instruction but using Adnawash as washing buffer. The cDNA obtained from these samples was analyzed by PCR for the EMT markers Twist, Akt2, PI3KCA and for the tumor stem cell markers ALDH1 and BMI1.

Figure 5:
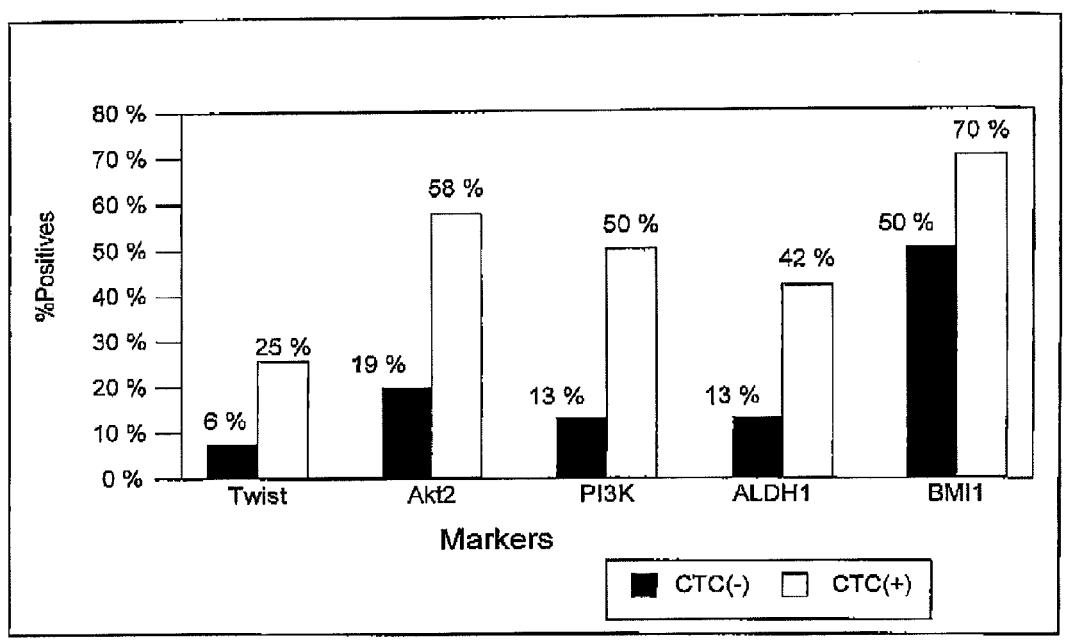
FIG. 5 shows the expression of EMT and tumor stem cell markers in patient samples in relation to the presence of CTC.

As is shown in FIG. 5, EMT and tumor stem cell markers are more frequently expressed in CTC(+) samples which are indicators for therapy resistance and bad prognosis in metastatic breast cancer than in CTC(−) samples As EMT and tumor stem cell markers correlate with CTC positivity they may be seen as a potential therapeutic or prognostic since they are associated with inferior prognosis and source of metastases. These over-expressed markers may serve as surrogate markers to stratify patients for personalized therapies.

EXAMPLE 7

The EMT marker Twist and the tumor stem cell markers ALDH1 and BMI1 were analyzed in metastatic breast cancer patients and correlated with therapy response. The samples were processed with the AdnaTest BreastCancerSelect reagents according to instructions but using AdnaWash as washing buffer. The cDNA obtained from these samples was analyzed by PCR for the EMT markers Twist as well as for the tumor stem cell markers ALDH1 and BMI1.

Figure 6:
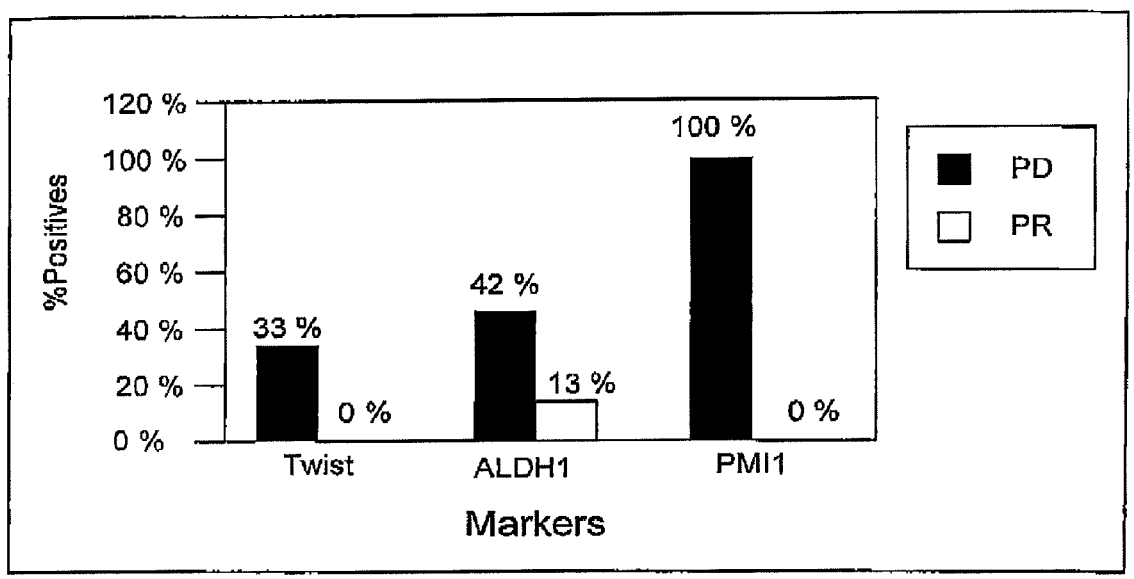
FIG. 6 shows the expression of EMT and tumor cell markers in patients in relation to therapy response. (PD: progressive disease; PR: partial remission/no change)

As shown in FIG. 6, Twist, ALDH1 and BMI1 are expressed in samples obtained using the AdnaTest BreastCancerSelect followed by RT-PCR. It can be shown, that patients not responding to a given therapy over-express the markers investigated more frequently than therapy responders (PD="progressive disease"; PR="partial remission as well as stop of progression").

As EMT and stem cell, markers Twist, ALDH1 and BMI1 are mainly expressed in CTC, they correlate furthermore with therapy failure in metastatic breast cancer if analysed with the method used in this invention. EMT and tumor stem cell markers can, therefore, be seen as a surrogate marker for therapy response but also as a therapeutic target to assess phenotypical changed CTC as sources of metastasis formation.

The invention claimed is:

1. A method for solid phase isolation, enrichment and/or detection of tumor stem cells and/or tumor cells in epithelial-mesenchymal transition (EMT) from a sample of body fluid containing such cells comprising (a) contacting the sample with a solid surface that preferentially binds the cells, and (b) then washing the solid surface to remove the sample, wherein the sample contains a polyol at least during step (a) or step (b), and in a detection step, detecting isolated or enriched cells by the expression of at least one marker associated with at least one of the group comprising tumor stem cells and tumor cells in epithelial-mesenchymal transition.

2. The method according to claim 1, wherein step (a) comprises an immunological selection of tumor cells.

3. The method according to claim 1, wherein before or during step (a), a polyol is added to the sample or solid phase.

4. The method according to claim 1, wherein the polyol is added to the sample or the solid phase or is present in the sample in a final concentration (V/V or W/V) selected from least 1%, at least 10%, at least 20%, at least 30%, at least 50% or at least 60%.

5. The method according to claim 1, wherein the polyol comprises at least one of the group of polyols comprising sorbitol, sucrose, trehalose, mannitol, fructose, malitol, lactitol, xylitol and glycerol.

6. The method according to claim 1, wherein the solid surface is at least one of a gel surface, a sepharose surface, a glass surface, a latex surface, a ceramics surface, a metal surface and a plastic surface.

7. The method according to claim 1, wherein the solid surface is the surface of magnetic beads.

8. The method according to claim 1, wherein ligands or antibodies that specifically bind to the cells are immobilized on the solid surface.

9. The method according to claim 1, wherein the body fluid is at least one of peripheral blood, bone marrow, urine, ascites, and sputum from a patient.

10. The method of claim 1, further comprising staging cancer and/or prognosing cancer and/or guiding tumor therapy.

11. The method of claim 1, further comprising contacting an isolated or enriched tumor stem cell and/or EMT tumor cell with a drug.

12. The method according to claim 1, wherein during or after step (a), a polyol is added to the solid phase or a washing buffer.

* * * * *